United States Patent
Horn et al.

(10) Patent No.: US 8,846,132 B2
(45) Date of Patent: Sep. 30, 2014

(54) METHOD FOR PRODUCING POLYMER LAYERS

(75) Inventors: Carina Horn, Biblis (DE); Joachim Hoenes, Zwingenberg (DE); Wolfgang-Reinhold Knappe, Ludwigshafen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1088 days.

(21) Appl. No.: 10/514,758

(22) PCT Filed: May 16, 2003

(86) PCT No.: PCT/EP03/05179
§ 371 (c)(1),
(2), (4) Date: Aug. 18, 2005

(87) PCT Pub. No.: WO03/097859
PCT Pub. Date: Nov. 27, 2003

(65) Prior Publication Data
US 2006/0099327 A1     May 11, 2006

(30) Foreign Application Priority Data

May 16, 2002 (DE) ................ 102 21 840
May 16, 2002 (DE) ................ 102 21 845
May 16, 2002 (DE) ................ 102 21 846

(51) Int. Cl.
*C12Q 1/00* (2006.01)
*C08F 2/48* (2006.01)
*G01N 33/543* (2006.01)
*C12Q 1/32* (2006.01)
*C12Q 1/26* (2006.01)

(52) U.S. Cl.
CPC ............ *C12Q 1/32* (2013.01); *G01N 33/54353* (2013.01); *C12Q 1/26* (2013.01); *C12Q 1/002* (2013.01); *G01N 33/54373* (2013.01)
USPC ................................. 427/8; 427/508

(58) Field of Classification Search
USPC ..................... 427/8, 487, 508, 517
See application file for complete search history.

(56) References Cited

U.S. PATENT DOCUMENTS 3,341,328 A * 9/1967 Schwerin et al. .......... 430/281.1
4,590,147 A * 5/1986 Lindley .................... 430/286.1
(Continued)

FOREIGN PATENT DOCUMENTS

EP         0 691 408 A1    1/1996
EP         0 691 408 B1    1/1996
(Continued)

OTHER PUBLICATIONS

English Translation of Corresponding JP Office Action dated Apr. 8, 2008.

*Primary Examiner* — Elena T Lightfoot
(74) *Attorney, Agent, or Firm* — Roche Diagnostics Operations, Inc.

(57) ABSTRACT

A method for producing a polymer layer on a transparent support. A photopolymerizable liquid composition is applied to the support. The photopolymerizable liquid composition is irradiated through the support such that polymerization of the liquid composition starts at the surface of the support and ends at a predetermined distance over the surface of the support. Only partial polymerization of the liquid composition takes place. A polymer layer with a predetermined thickness is formed on the support wherein the predetermined thickness is less than the thickness of the photopolymerizable liquid composition. The remaining photopolymerizable liquid composition is removed from the entire polymer layer.

7 Claims, 4 Drawing Sheets

(56) References Cited

U.S. PATENT DOCUMENTS

| | | |
|---|---|---|
| 5,296,305 A | 3/1994 | Baude et al. |
| 5,407,818 A | 4/1995 | Von Gentzkow et al. |
| 5,663,042 A * | 9/1997 | Grieve et al. ............. 430/619 |
| 5,691,205 A | 11/1997 | Kawabata et al. |
| 5,693,034 A | 12/1997 | Buscemi et al. |
| 5,863,650 A | 1/1999 | Healy et al. |
| 6,030,749 A * | 2/2000 | Takahashi ............. 430/273.1 |
| 6,613,282 B2 | 9/2003 | Huber et al. |
| 2002/0006588 A1 * | 1/2002 | Afromowitz ............. 430/322 |
| 2002/0123134 A1 * | 9/2002 | Huang et al. ............. 435/287.2 |
| 2003/0087178 A1 * | 5/2003 | Lungu ............. 430/162 |

FOREIGN PATENT DOCUMENTS

| | | |
|---|---|---|
| JP | 63273609 A | 11/1988 |
| WO | 00/42438 A1 | 7/2000 |
| WO | WO 02/052045 A | 7/2002 |

* cited by examiner

METHOD FOR PRODUCING POLYMER LAYERS

CROSS-REFERENCE TO RELATED APPLICATIONS

This application is a National Stage of International Application No. PCT/EP03/05179, filed May 16, 2003, which claims the benefit and priority of German Patent Application Nos. 102 21 840.4, 102 21 845.5 and 102 21 846.3, filed May 16, 2002. The entire disclosures of each of the above applications are incorporated herein by reference.

BACKGROUND

The invention relates to a method for producing polymer layers on a support by photopolymerization of a polymerizable liquid composition, to a device which is suitable for producing polymer layers on a support, and to a method for producing a sensor which comprises a polymer layer with an indicator embedded therein.

The production of polymer layers on supports is known. For this purpose, a polymerizable liquid is applied in a thickness which is as uniform as possible onto the support and completely polymerized. The polymerization can be started by chemical polymerization initiators or by irradiation of the liquid.

Polymerization techniques known in connection with the production of adhesive films entail a mixture of functionalized acrylate prepolymers being applied to a support and being wholly or partly cured by irradiation of the surface of the polymer composition. The layer thickness of the polymerization is controlled through choice of the intensity and duration of illumination and through the intrinsic absorption of the prepolymers employed.

A disadvantage of the prior art methods is that adjustment of a predetermined and uniform thickness of the polymer layer on the support is often necessarily very complicated. In addition, with conventional polymerization methods the adhesion of the polymer layer to the support is often only low.

SUMMARY

The object on which the present invention is based was to avoid at least in part the prior art disadvantages described. It was particularly intended to provide a method for producing polymer layers on a support, which makes it possible in a simple manner to produce polymer layers with a predetermined and uniform layer thickness.

In contrast to the methods described in the prior art in connection with adhesive production, in which closed, hydrophobic polymer layers are produced, the intention is to provide open, hydrophilic layers able to absorb aqueous sample liquid and analyte.

This object is achieved by a liquid polymerizable composition being applied to a support and there being polymerized directly on the support, not completely but only in a layer of predetermined thickness. It is possible in this way to produce uniform supports of the layers which adhere very well to the support in a simple manner.

One aspect of the invention is thus a method for producing polymer layers on a transparent support, comprising the steps:
(a) provision of a support,
(b) application of a photopolymerizable liquid composition to the support,
(c) irradiation of the photopolymerizable liquid composition through the support in such a way that only partial polymerization of the liquid composition takes place, and a polymer layer with a predetermined thickness is formed on the support, and
(d) removal of the remaining liquid composition from the polymer layer.

The support used to produce polymer layers is an at least partly optically transparent support, for example a plastics support such as, for example, polycarbonate sheet, cellulose acetate sheet, polyester sheet or polyether sheet, a glass support or a quartz support. It is also possible to employ supports of composite materials. When such an at least partly optically transparent support is used, the liquid composition is preferably irradiated through the support. The thickness of the support is favorably chosen so as to provide firstly an adequate mechanical stability for the polymer layer and secondly an adequate transparency for the light used for the irradiation. For example, supports with a thickness of from 5 μm to 20 mm are used. It is likewise preferred to use UV-transparent supports.

The photopolymerizable liquid composition comprises at least one photopolymerizable substance, i.e. a substance which is polymerizable by irradiation (where appropriate in the presence of a photoinitiator). Preferred examples of such substances are photopolymerizable monomers such as, for example, olefinically unsaturated substances, i.e. substances having a C=C linkage. Further examples of suitable photopolymerizable substances are functionalized oligomers or polymers which crosslink on irradiation with light. Such photoactive functionalizations include, for example, acrylates, azides, carbazides, sulfonazides, diazo ketones, dimethylmaleimides, photocyclizable radicals (e.g. chalcones) and benophen derivatives. Examples of suitable oligomers or polymers are polyurethanes, polyvinyl alcohols, polyesters, polyethers, polyvinylpyrolidones, polyacrylates or oligosaccharides. The photopolymerizable substances are particularly preferably selected from acrylic monomers such as, for example, acrylamide, arcyl esters, e.g. polyethylene glycol diacrylate, vinylaromatic monomers such as, for example, 4-vinylbenzenesulfonic acid, functionalized polyvinylpyrolidones and any combinations of one or more of said substances.

In a preferred embodiment, an aqueous polymerizable composition in which the monomers to be polymerized are present in dissolved form is used. It is therefore expedient to employ for this embodiment hydrophilic monomers which have sufficiently high solubility in an aqueous solvent.

The polymerization in the liquid composition is initiated by irradiation with light. The composition preferably comprises one or more photoinitiators in order to induce polymerization. Examples of suitable photoinitiators are free-radical initiators such as benzophenones, benzils, anthraquinones, thiosulfonic acids, azo compounds, or ionic initiators such as, for example, triarylsulfonium salts, arylium hexafluoro-antimonates.

The irradiation of the composition takes place through the support so that the polymerization starts at the surface of the support and—depending on the set polymerization conditions—ends at a predetermined distance over the surface of the support because of the light absorption within the polymerizable liquid. Distortions or deviations from the horizontal position in the support cannot influence the thickness of the polymer layer. Mechanical tolerances are substantially eliminated.

The thickness of the polymer layer can be adjusted in a wide range by suitable measures. In particular, the layer thickness of the polymer can be controlled by varying the intensity of irradiation, the duration of irradiation or/and the addition of polymerization inhibitors, e.g. UV-absorbing substances, to the liquid composition. Control is also possible through the thickness of the support or/and the material of the support. The thickness of the polymer layers is preferably ≤500 μm and particularly preferably ≤100 μm. When the polymer layers are used as sensors, in particular as biosensors, lower layer thicknesses of, preferably, ≤50 μm, in particular of ≤5 μm, are often also produced.

If the polymer layer is to be employed as component of a sensor, it expediently comprises an indicator, besides the components already mentioned, e.g. an optical or/and electrochemical indicator able to respond to parameters in the medium surrounding the polymer layer. The indicator may be added to the photopolymerizable liquid composition or—especially when it is a relatively small molecule—be diffused into the already complete polymer layer. If the polymer layer is to comprise a plurality of indicators, combinations of the aforementioned measures are also possible.

The indicator may also be a macromolecule, for example is with a molecular weight of ≥10 kD and in particular of ≥20 kD. A catalytic substance is particularly preferably used as indicator, for example an enzyme which may where appropriate be present in the form of an enzyme-coenzyme complex. Particular preferred examples of enzymes are oxidoreductases, especially dehydrogenases, such as, for example, glucose dehydrogenase (E.C.1.1.1.47) or oxidases. Coenzymes are preferably organic molecules which are linked covalently or noncovalently to an enzyme and are altered, for example oxidized or reduced, through the reaction with a substrate of the enzyme. Preferred examples of coenzymes are flavin, nicotine, quinone derivatives such as, for example, FAD, $FADH_2$, $NAD^+$, $NADH/H^+$, $NADP^+$, $NADPH/H^+$ or PQQ.

The polymer layer may, besides enzymes and where appropriate coenzymes, also comprise mediators, i.e. substances able to bring about regeneration of coenzymes. In this case, the enzyme acts as catalytic indicator, i.e. it is able to convert a plurality of molecules of a substrate, for example of an analyte present in the added sample, such as, for example, glucose in the blood.

In a particularly preferred embodiment, the polymer layer comprises an enzyme-coenzyme complex as stoichiometric reactant for an enzyme substrate to be detected. In this case, the coenzyme is converted once and not regenerated. It is no longer necessary in this embodiment to use mediators associated with the use of complex reagent mixtures of low stability and high susceptibility to interference.

When macromolecular substances are used as indicators it is possible by suitable crosslinking of the polymer (e.g. through use of bifunctional or/and polyfunctional monomers) to produce a crosslinked polymer layer in which the macromolecular indicator substance is embedded in immobilized form, while low molecular weight substances such as, for example, coenzyme, enzyme substrate etc. can diffuse into the layer.

Production of the polymer layer can be carried out as continuous process, in which case there is continuous formation of a polymer layer in a liquid photopolymerizable composition applied to a support. In the continuous polymerization, the photopolymerizable liquid composition is preferably continuously applied at a first position to a moving support and continuously irradiated at a second position. It is, of course, also possible for the support to be held stationary and for the positions of the liquid application and of irradiation to be moved. Discontinuous methods for producing the polymer films are likewise conceivable. It is common to these embodiments that, owing to the irradiation of the photopolymerizable liquid compositions through the support, it is possible for the polymerization of the liquid to start directly on the support and not be complete.

Yet a further aspect of the invention is a device for producing polymer layers, comprising
(a) means for receiving and where appropriate for transporting a support,
(b) means for applying a photopolymerizable liquid composition to the support and
(c) means for irradiating the photopolymerizable liquid composition through the support in order to form a polymer layer with predetermined thickness on the support, and
(d) where appropriate means for removing unpolymerized liquid composition from the polymer layer.

The method and the device can be used to produce a sensor, in which case an indicator, for example a biomolecule such as, for example, an enzyme, is embedded in the polymer layer. The indicator can be present in the polymer layer in immobilized form. The indicator is particularly preferably an enzyme, where appropriate in the form of an enzyme-coenzyme complex. The sensor may be for example an optical or/and electrochemical sensor. The sensor is particularly preferably a fluorescence-based sensor.

Yet a further aspect of the invention is a method for producing a sensor, comprising the steps:
(a) provision of a support,
(b) application of a photopolymerizable liquid composition which comprises at least one indicator to the support,
(c) irradiation of the photopolymerizable liquid composition through the support in such a way that a polymer layer with a predetermined thickness is formed on the support,
(d) removal of the remaining liquid composition from the polymer layer and
(e) introduction of the support with the polymer layer comprising the indicator into a sensor which comprises means for detecting the reaction of the indicator with an analyte in a sample.

The detection means are, in particular, optical or/and electrochemical detection means. The detection means are particularly preferably optical detection means comprising a light source for irradiating the polymer layer and a detector for collecting light from the polymer layer. The light source, e.g. a laser or an LED, is preferably provided to beam light through the support into the polymer layer. The detector is preferably provided for collecting light radiation, e.g. fluorescence emission, from the polymer layer.

The sensor may be used to determine any analytes, for example physicochemical parameters such as, for example, temperature, partial pressures of gases such as, for example, $O_2$, $CO_2$, $NO_x$ etc., or to determine biochemical parameters such as, for example, analytes in biological samples, e.g. body fluids.

The invention is additionally to be explained by the following figures and examples.

BRIEF DESCRIPTION OF DRAWINGS

The drawings described herein are for illustrative purposes only of selected embodiments and not all possible implementations, and are not intended to limit the scope of the present disclosure.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

Figure 1:
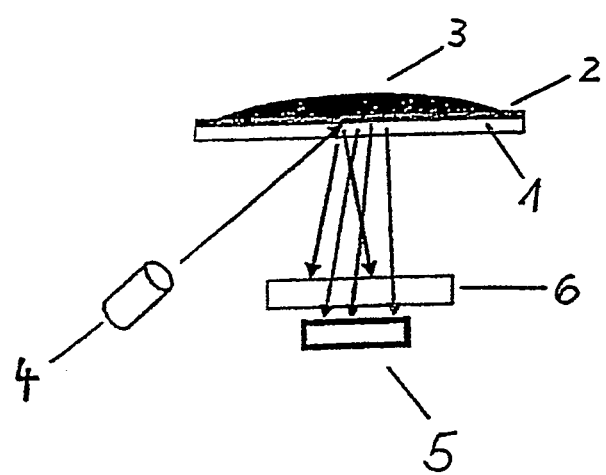
FIG. 1 illustrates a schematic view of an exemplary sensor made in accordance with the present teachings.

FIG. 1 shows a first embodiment of a sensor produced by the method of the invention. A polymer layer (2) with an indicator, e.g. with a detection reagent for an enzymatic reaction, is applied to an optically transparent support (1). A sample (3), e.g. blood, is put onto the polymer layer. Determination of the enzymatic reaction between the analyte present in the sample (3), and the detection reagent present in the polymer layer (2) takes place by optical methods. Light from a light source (4), e.g. a laser or an LED, is beamed in from below (through the support) onto the reagent layer (2). Absorption light or fluorescent light radiated back from the sample is detected in a detector (5). Where appropriate—especially for detecting fluorescent light—an optical filter element (6) is put in front of the detector in order to block leakage of the fluorescence-exciting light.

Figure 2:
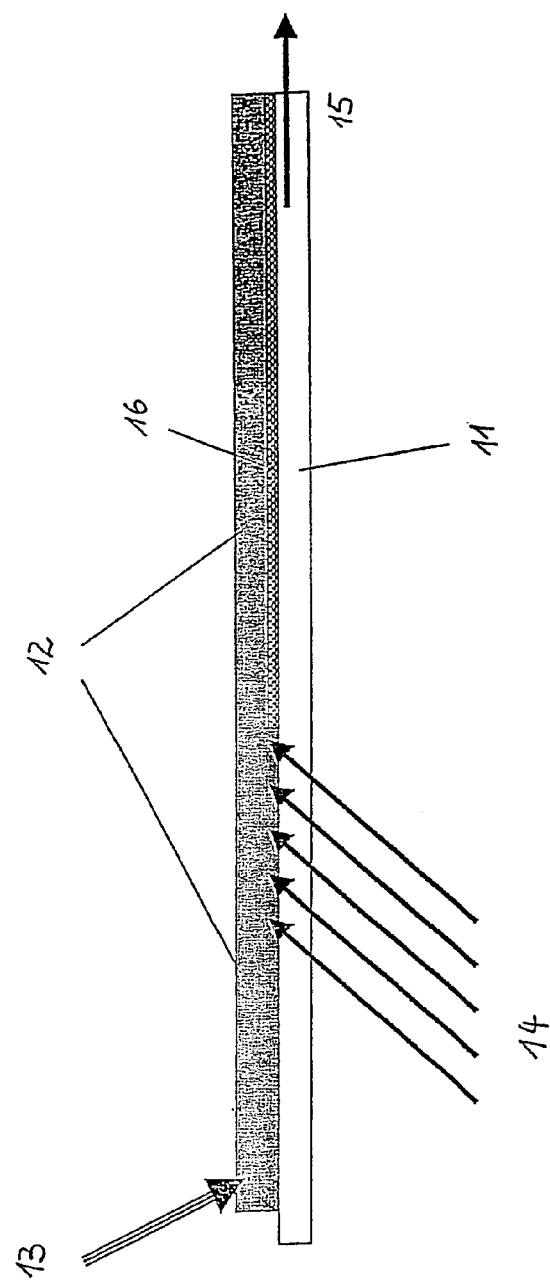
FIG. 2 illustrates a polymer layer provided over a transparent support in accordance with the present teachings.

FIG. 2 shows the production of a polymer layer of the invention. A liquid reagent (12) is applied, for example in a first position (13), to an optically transparent support (11), e.g. a plastics sheet. The liquid reagent (12) is irradiated at a second position from below through the support (11) with light from a light source (14). At the same time, the support is moved in the direction (15) identified by the arrow. A polymerized reagent layer (16) is formed directly on the support (11). Excess liquid reagent is present above the polymer layer (16). The thickness of the polymerized reagent layer (16) can be controlled through the reagent composition, the duration and intensity of the beaming in of light, and through the properties of the support (11).

Figure 3:
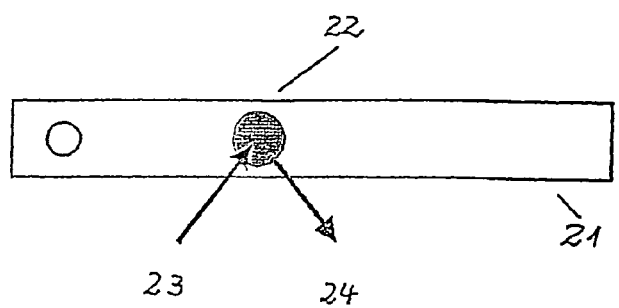
FIG. 3 illustrates a fluorescence based sensor in accordance with the present teachings.

FIG. 3 shows an embodiment of a fluorescence-based sensor from below. A polymer layer, for example one produced by the continuous process in FIG. 2, comprising an indicator can be cut and introduced into a sensor (21) by use of known techniques. After application of the sample to the upper side, exciting light (23), e.g. UV light, is beamed in from a light source from below. The fluorescence (24), e.g. blue light, generated through the reaction of the analyte with the detection reagent in the polymer layer (22) is detected with a detector.

Figure 4:
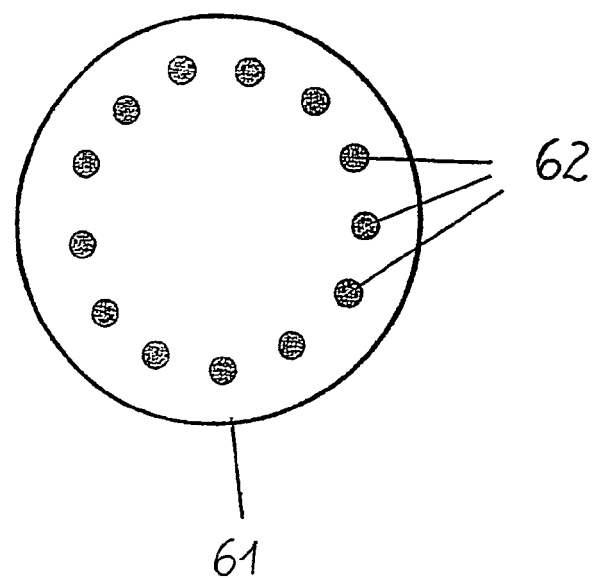
FIG. 4 illustrates a plurality of reagent spots disposed on a transparent support in accordance with the present teachings.

It is also possible to apply a plurality of (identical or different) reagents to a support. One example of such an embodiment in the form of a disc is shown in FIG. 4. A plurality of reagent spots (62) consisting of polymer layers with indicators is disposed on the optically transparent support (61).

EXAMPLES

Example 1

Detection of Glucose in the Glucose Dehydrogenase (GlucDH)NAD$^+$ System in a Polymer Film A suspension of the following substance was mixed in a plastic test tube.

Formula 1

| Substance | Amount [g] | Weight [%] |
|---|---|---|
| Acrylamide | 2.5 | 22.02 |
| Methylenebisacrylamide | 0.7 | 6.17 |
| 2,2-Dimethoxy-2-phenylacetophenone | 0.05 | 0.44 |
| Glycerol | 5 | 44.05 |
| Hydroxyethyl methacrylate | 1.4 | 12.33 |
| Methyl methacrylate | 0.4 | 3.52 |
| Crodasinic O solution, pH 8, 0.3 g/1000 ml | 1 | 8.81 |
| N,N'-(1,2-Dihydroxyethylene)bisacrylamide | 0.3 | 2.64 |
| TOTAL | 11.35 | 100 |

0.5 ml of this suspension were mixed with 0.5 ml of a solution of GlucDH (100 mg/ml), and the mixture was homogenized free of air bubbles in an ultrasonic bath.

The clear solution was poured onto a corona-treated sheet (?) and illuminated with a conventional illumination apparatus (Isel UV illumination device 2) through the support for 20 min. The sheet was briefly washed with water and then dried in the air.

The resulting layer thickness was <2 μm. A freshly prepared glucose/NAD$^+$ solution (GKL-3 solution, 300 mg/dl glucose, 1 ml/6.4 mg of NAD$^+$) was spotted on the film. A strong fluorescence was immediately visible under a UV lamp.

Example 2

Adding a UV Absorber to Influence the Layer Thickness

A polymer layer comprising a blue dye (absorption maximum ≈650 nm) for better identification was produced (formula 2). In a further experiment, a yellow dye was admixed as UV absorber to the initial formula (formula 3).

Formula 2

| Substance | Amount | Weight [%] |
|---|---|---|
| Acrylamide | 37.5 g (0.53 mol) | 25.78 |
| Polyethylene glycol diacrylate, Mw ≈ 575 g/mol | 52.5 g (ca. 0.96 mol) | 36.10 |
| Solution of Crodasinic O (0.3 g/1 l) | 50 g | 34.38 |
| 4-Vinylbenzenesulfonic acid | 5 g | 3.44 |
| 2,2-Dimethoxy-2-phenylacetophenone photoinitiator | 350 mg | 0.24 |
| New methylene blue N | 100 mg | 0.06 |
| TOTAL | 145.45 g | 100 |

The mixture was homogenized by stirring and by ultrasonic bath treatment, distributed with pipette on a 140 μm Pokalon sheet (corona-treated, stage 4) and illuminated in a UV illumination device (Actina U4, W. Lemmen GmbH) for 1 min.

The resulting layer thickness was measured with a screw gage and was 240.5 μm.

| Formula 3 | | |
|---|---|---|
| Substance | Amount | Weight [%] |
| Formula 2 | 1 ml | ca. 99.99 |
| Mordant Yellow 7 (No. 686) (UV absorber) | 0.0001 g | 0.001 |
| TOTAL | c. 1.0001 g | 100 |

The mixture was distributed on a sheet and then polymerized as described above. The resulting layer thickness was measured with a screw gage and was 79.3 μm.

This experiment shows that it is possible to influence the layer thickness. With reaction conditions which were otherwise the same, the layer thickness without UV absorber is 240.5 μm (see above); only 79.3 μm with UV absorber (Mordant Yellow 7).

What is claimed is:

1. A method for producing a polymer layer on a transparent support, comprising:
    (a) applying of a layer of an aqueous photopolymerizable liquid composition to the support,
    (b) irradiating the aqueous photopolymerizable liquid composition through the support, forming a polymer layer having a predetermined thickness on the support wherein the predetermined thickness is less than the thickness of the layer of photopolymerizable liquid composition; and
    (c) removing remaining aqueous photopolymerizable liquid composition from the polymer layer;
wherein the polymer layer comprises an indicator comprising an enzyme.

2. The method of claim 1, wherein the polymer layer has a uniform thickness.

3. The method of claim 1, wherein the indicator responds optically or electrochemically to a medium placed in contact with the polymer layer.

4. A method for producing a polymer layer on a transparent support, consisting of:
    (a) applying of a layer of an aqueous photopolymerizable liquid composition to the support,
    (b) irradiating the aqueous photopolymerizable liquid composition through the support, forming a polymer layer having a predetermined thickness on the support wherein the predetermined thickness is less than the thickness of the layer of photopolymerizable liquid composition; and
    (c) removing remaining photopolymerizable liquid composition from the polymer layer.

5. The method of claim 4, wherein the polymer layer comprises an indicator comprising an enzyme.

6. The method of claim 4, wherein the polymer layer has a uniform thickness.

7. The method of claim 5, wherein the indicator responds optically or electrochemically to a medium placed in contact with the polymer layer.

* * * * *